US00PP20019P2

(12) United States Plant Patent
Wood

(10) Patent No.: US PP20,019 P2
(45) Date of Patent: May 26, 2009

(54) ***HYDRANGEA* PLANT NAMED 'LYNN'**

(50) Latin Name: *Hydrangea macrophylla*
Varietal Denomination: Lynn

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/075,448

(22) Filed: Mar. 11, 2008

(51) Int. Cl.
*A01H 5/00* (2006.01)

(52) U.S. Cl. ..... Plt./250

(58) Field of Classification Search ..... Plt./250
See application file for complete search history.

*Primary Examiner*—S. B. McCormick Ewoldt
(74) *Attorney, Agent, or Firm*—C. A. Whealy

(57) ABSTRACT

A new and distinct cultivar of *Hydrangea* plant named 'Lynn', characterized by its upright and mounded plant habit; strong roots and stems; strong and dark green-colored leaves; and large lacecap-type inflorescences with intense pink-colored flowers.

1 Drawing Sheet

Figure 1:
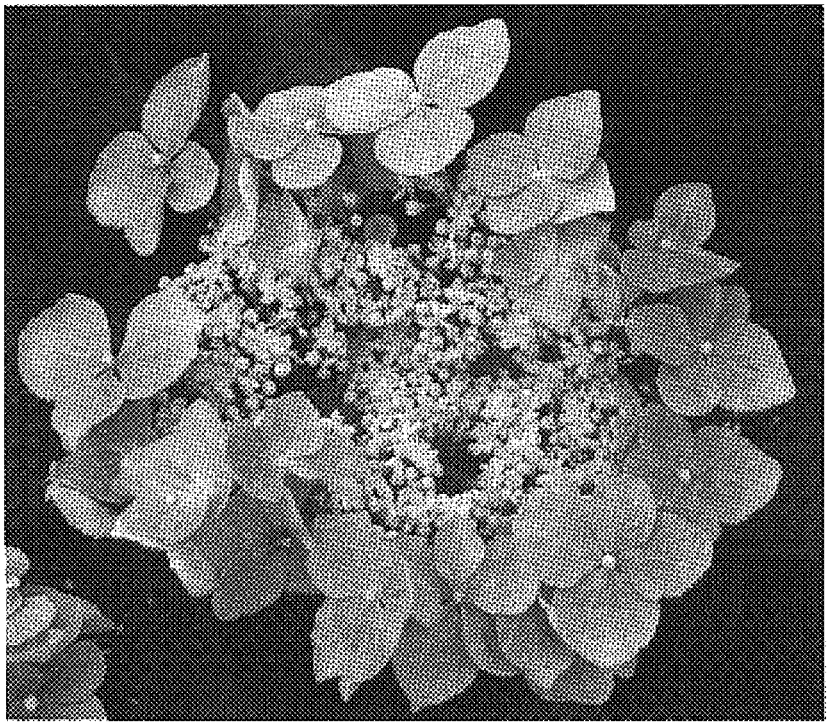
Figure 2:
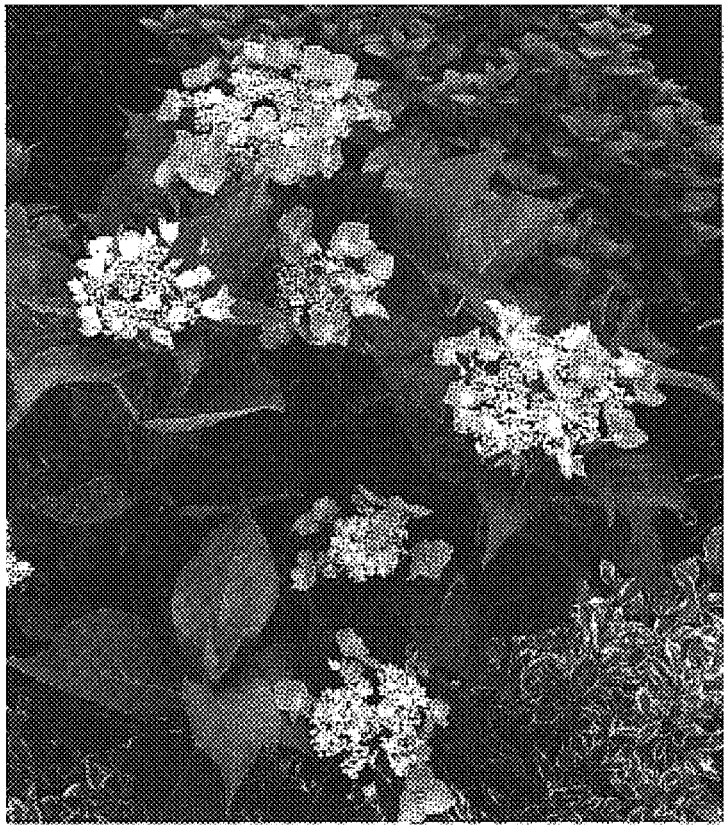

Botanical designation: *Hydrangea macryophylla.*
Cultivar denomination: 'LYNN'.

BACKGROUND OF THE INVENTION

The present invention relates to a new and distinct cultivar of *Hydrangea,* botanically known as *Hydrangea macrophylla* and hereinafter referred to by the name 'Lynn'.

The new *Hydrangea* is a product of a planned breeding program conducted by the Inventor in Grand Haven, Mich. The objective of the breeding program was to develop new *Hydrangeas* with attractive foliage and flower coloration.

The new *Hydrangea* originated from an open-pollination in July, 2003 of the *Hydrangea macrophylla* cultivar Bailmer, disclosed in U.S. Plant Pat. No. 15,298, as the female, or seed parent and an unknown selection of *Hydrangea macrophylla.* The cultivar Lynn was discovered and selected by the Inventor in May, 2005 as a flowering plant within the progeny of the stated open-pollination in a controlled environment in Grand Haven, Mich.

Asexual reproduction of the new cultivar by softwood cuttings in Grand Haven, Mich. since June, 2005 has shown that the unique features of this new *Hydrangea* plant are stable and reproduced true to type in successive generations of asexual reproduction.

SUMMARY OF THE INVENTION

The cultivar Lynn has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Lynn'. These characteristics in combination distinguish 'Lynn' as a new and distinct cultivar of *Hydrangea:*

1. Upright and mounded plant habit.
2. Strong roots and stems.
3. Strong and dark green-colored leaves.
4. Large lacecap-type inflorescences with intense pink-colored flowers.

Plants of the new *Hydrangea* differ from plants of the female parent, the cultivar Bailmer, in the following characteristics:

1. Plants of the new *Hydrangea* have darker green-colored leaves than plants of the cultivar Bailmer.
2. Plants of the new *Hydrangea* have lacecap-type inflorescences whereas plants of the cultivar Bailmer have mophead-type inflorescences.
3. Flowers of plants of the new *Hydrangea* have larger sepals than flowers of plants of the cultivar Bailmer.
4. Sepals of plants of the new *Hydrangea* are brighter pink in color than sepals of plants of the cultivar Bailmer.

Plants of the new *Hydrangea* can be compared to plants of the cultivar Kardinal, not patented. Plants of the new *Hydrangea* differ from plants of the cultivar Kardinal in the following characteristics:

1. Plants of the new *Hydrangea* have smaller and darker green-colored leaves than plants of the cultivar Kardinal.
2. Plants of the new *Hydrangea* have broader, but shorter inflorescences than plants of the cultivar Kardinal.
3. Plants of the new *Hydrangea* do not require vernalization treatments to flower whereas plants of the cultivar Kardinal require vernalization treatments to flower.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new *Hydrangea.*

The photograph at the bottom of the sheet comprises a side perspective view of a typical flowering plant of 'Lynn' grown in an outdoor nursery.

The photograph at the top of the sheet is a close-up view of a typical inflorescence of 'Lynn'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and in the following description were grown in Grand Haven, Mich. in ground beds in an outdoor nursery and under conditions which closely approximate commercial production conditions. Plants of the new *Hydrangea* were about 2.5 years old when the photographs and description were taken during the summer.

Botanical description: *Hydrangea macrophylla* cultivar Lynn.

Parentage:

*Female, or seed, parent.*—*Hydrangea macrophylla* cultivar Bailmer, disclosed in U.S. Plant Pat. No. 15,298.

*Male, or pollen, parent.*—Unknown selection of *Hydrangea macrophylla,* not patented.

Propagation:

*Type cutting.*—By softwood cuttings.

*Time to initiate roots.*—About ten days at temperatures of about 24° C.

*Time to produce a rooted young plant.*—About 40 days at temperatures of about 24° C.

*Root description.*—Fine, fibrous.

*Rooting habit.*—Freely branching; dense.

Plant description:

*Form/growth habit.*—Perennial shrub. Upright and mounded plant habit; broadly inverted triangle. Strong lateral branches; vigorous growth habit.

*Plant height.*—About 59 cm.

*Plant diameter or area of spread.*—About 75 cm.

*Branching habit.*—When pinched, freely branching with about seven lateral branches per plant.

*Lateral branches.*—Length: About 55 cm. Diameter: About 7 mm. Internode length: About 8 cm. Texture: Smooth, glabrous. Strength: Strong. Color: 144B with speckles, 59A.

Foliage description:

*Arrangement.*—Opposite, simple.

*Length.*—About 14 cm.

*Width.*—About 9 cm.

*Shape.*—Oblanceolate.

*Apex.*—Acute.

*Base.*—Cuneate.

*Margin.*—Serrate.

*Texture, upper and lower surfaces.*—Rugose; glabrous.

*Venation pattern.*—Pinnate.

*Color.*—Developing foliage, upper and lower surfaces: 143C. Fully expanded foliage, upper and lower surfaces: 137A; venation, 143C.

*Petiole.*—Length: About 3.2 cm. Diameter: About 4 mm. Texture, upper and lower surfaces: Smooth, glabrous. Color, upper and lower surfaces: 143C.

Flower description:

*Flower type and habit.*—Single sterile and fertile flowers arranged on terminal lacecap-type panicles. Flowers face upright or outward. Flowers not fragrant.

*Natural flowering season.*—Continuous flowering from June to August in Grand Haven, Mich. Plants begin flowering about 105 days after pinching.

*Flower longevity, fertile flowers.*—Flowers last about two to three weeks on the plant and about two weeks as a cut flower; flowers not persistent.

*Flower longevity, sterile flowers.*—Flowers last about three months on the plant and about three weeks as a cut flower; flowers persistent.

*Quantity of flowers.*—Freely flowering; about 337 fertile flowers and about 30 sterile flowers per panicle.

*Panicle height.*—About 9.5 cm.

*Panicle diameter.*—About 25 cm.

*Flower diameter, fertile flowers.*—About 9 mm.

*Flower depth (height), fertile flowers.*—About 5 mm.

*Flower diameter, sterile flowers.*—About 6.5 cm.

*Flower depth (height), sterile flowers.*—About 7 cm.

*Flower buds, fertile and sterile flowers.*—Length: About 3 mm. Diameter: About 3 mm. Shape: Globular. Color: 62B.

*Petals, fertile flowers only.*—Arrangement: Four in a single whorl. Length: About 4 mm. Width: About 2 mm. Shape: Lanceolate, cupped. Apex: Acute. Base: Attenuate. Margin: Entire. Texture, upper and lower surfaces: Smooth, glabrous. Color: When opening and fully opened, upper surface: 62B. When opening and fully opened, lower surface: 62B.

*Sepals, fertile flowers.*—Quantity per flower: Five in a single whorl. Length: About 1 mm. Width: About 0.5 mm. Shape: Deltoid. Apex: Acute. Base: Truncate. Margin: Entire. Texture, upper and lower surfaces: Smooth, glabrous. Color: When opening, upper and lower surfaces: 42B. Fully opened, upper and lower surfaces: 42B.

*Sepals, sterile flowers.*—Quantity per flower: Four in a single whorl. Length: About 2.5 cm. Width: About 3 cm. Shape: Broadly ovate. Apex: Broadly acute. Base: Broadly cuneate. Margin: Entire to slightly serrated. Texture, upper and lower surfaces: Smooth, glabrous. Color: When opening and fully opened, upper surface: 66B. When opening and fully opened, lower surface: 66D.

*Peduncles, fertile and sterile flowers.*—Angle: Erect to about 15° from vertical. Strength: Strong. Length: About 6.2 cm. Diameter: About 4 mm. Texture: Smooth, glabrous. Color: 59C.

*Pedicels, fertile flowers.*—Angle: Erect to about 15° from vertical. Strength: Strong. Length: About 5 mm. Diameter: About 1 mm. Texture: Smooth, glabrous. Color: 59C.

*Pedicels, sterile flowers.*—Angle: About 10° to about 20° from vertical. Strength: Strong. Length: About 2.5 cm. Diameter: About 2 mm. Texture: Smooth, glabrous. Color: 65C.

*Reproductive organs, fertile flowers only.*—Stamens: None observed. Pistils: Pistil quantity per flower: About four. Pistil length: About 7 mm. Stigma shape: Round. Stigma color: 65C. Style length: About 2 mm. Style color: 42B to 42C. Ovary color: 42B.

*Seeds.*—Quantity per inflorescence: Numerous. Size: Less than 0.1 mm by less than 0.1 mm. Color: Close to 200D.

Disease/pest resistance: Plants of the new *Hydrangea* have been observed to be resistant to Powdery Mildew. Plants of the new *Hydrangea* have not been observed to be resistant to pests or other pathogens common to *Hydrangea.*

Temperature tolerance: Plants of the new *Hydrangea* have been shown to be tolerant to temperatures ranging from about −27° C. to about 37° C.

It is claimed:

1. A new and distinct *Hydrangea* plant named 'Lynn' as illustrated and described.

* * * * *